(12) United States Patent
Bonn

(10) Patent No.: US 8,059,059 B2
(45) Date of Patent: Nov. 15, 2011

(54) SLIDABLE CHOKE MICROWAVE ANTENNA

(75) Inventor: Kenlyn Bonn, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 485 days.

(21) Appl. No.: 12/129,482

(22) Filed: May 29, 2008

(65) Prior Publication Data

US 2009/0295674 A1  Dec. 3, 2009

(51) Int. Cl.
 *A61B 18/18* (2006.01)
 *H01Q 1/42* (2006.01)
 *H01Q 9/04* (2006.01)
(52) U.S. Cl. .................. 343/872; 343/793; 606/33
(58) Field of Classification Search .............. 343/872; 606/33
See application file for complete search history.

(56) References Cited

U.S. PATENT DOCUMENTS

| | | | |
|---|---|---|---|
| 3,230,957 A | 1/1966 | Seifert |
| 3,631,363 A | 12/1971 | Miller |
| 4,557,272 A | 12/1985 | Carr |
| 4,612,940 A | 9/1986 | Kasevich et al. |
| 4,643,186 A | 2/1987 | Rosen et al. |
| 4,658,836 A | 4/1987 | Turner |
| 4,674,481 A | 6/1987 | Boddie, Jr. et al. |
| 4,700,716 A | 10/1987 | Kasevich et al. |
| 4,743,725 A | 5/1988 | Risman |
| 4,776,086 A | 10/1988 | Kasevich et al. |
| 4,798,215 A | 1/1989 | Turner |
| 4,800,899 A | 1/1989 | Elliott |
| 4,807,620 A | 2/1989 | Strul et al. |
| 4,817,635 A | 4/1989 | Joines et al. |
| 4,825,880 A | 5/1989 | Stauffer et al. |
| 4,841,988 A | 6/1989 | Fetter et al. |
| 4,934,365 A | 6/1990 | Morgenthaler |
| 4,945,912 A | 8/1990 | Langberg |
| 5,026,959 A | 6/1991 | Ito et al. |
| 5,057,106 A | 10/1991 | Kasevich et al. |
| 5,065,819 A | 11/1991 | Kasevich |
| 5,097,845 A | 3/1992 | Fetter et al. |
| 5,097,846 A | 3/1992 | Larsen |
| 5,129,396 A | 7/1992 | Rosen et al. |
| 5,190,054 A | 3/1993 | Fetter et al. |
| 5,246,438 A | 9/1993 | Langberg |

(Continued)

FOREIGN PATENT DOCUMENTS

DE  390937  3/1924

(Continued)

OTHER PUBLICATIONS

International Search Report PCT/US98/23950 dated Jan. 14, 1998.

(Continued)

*Primary Examiner* — Trinh V Dinh

(57) ABSTRACT

A microwave antenna assembly is disclosed. The antenna assembly includes a feedline having an inner conductor, an outer conductor and an inner insulator disposed therebetween and a radiating portion including a dipole antenna coupled to the feedline and a trocar coupled to the dipole antenna at a distal end thereof. The antenna assembly also includes a slidable outer jacket disposed about the radiating portion and the feedline. The slidable outer jacket being configured to slide about at least one of the radiating portion and the feedline from a closed configuration, in which the slidable outer jacket is mated with the trocar and a retracted configuration, in which the slidable outer jacket is retracted in a proximally exposing at least a portion the radiating portion.

7 Claims, 15 Drawing Sheets

U.S. PATENT DOCUMENTS

| | | |
|---|---|---|
| 5,281,217 A | 1/1994 | Edwards et al. |
| 5,300,068 A | 4/1994 | Rosar et al. |
| 5,301,687 A | 4/1994 | Wong et al. |
| 5,330,518 A | 7/1994 | Neilson et al. |
| 5,344,441 A | 9/1994 | Gronauer |
| 5,358,515 A | 10/1994 | Hurter et al. |
| 5,369,251 A | 11/1994 | King et al. |
| 5,370,644 A | 12/1994 | Langberg |
| 5,405,346 A | 4/1995 | Grundy et al. |
| 5,549,639 A | 8/1996 | Ross |
| 5,658,278 A | 8/1997 | Imran et al. |
| 5,776,176 A | 7/1998 | Rudie |
| 5,861,021 A | 1/1999 | Thome et al. |
| 5,871,523 A | 2/1999 | Fleischman et al. |
| 5,871,525 A | 2/1999 | Edwards et al. |
| 5,904,709 A | 5/1999 | Arndt et al. |
| 5,938,692 A | 8/1999 | Rudie |
| 5,944,749 A | 8/1999 | Fenn |
| 5,957,922 A | 9/1999 | Imran |
| 5,957,969 A | 9/1999 | Warner et al. |
| 5,964,755 A | 10/1999 | Edwards |
| 6,016,452 A | 1/2000 | Kasevich |
| 6,019,757 A | 2/2000 | Scheldrup |
| 6,026,331 A | 2/2000 | Feldberg et al. |
| 6,134,476 A | 10/2000 | Arndt et al. |
| 6,210,367 B1 | 4/2001 | Carr |
| 6,245,062 B1 | 6/2001 | Berube et al. |
| 6,287,302 B1 | 9/2001 | Berube |
| 6,289,249 B1 | 9/2001 | Arndt et al. |
| 6,312,427 B1 | 11/2001 | Berube et al. |
| 6,312,428 B1 | 11/2001 | Eggers et al. |
| 6,325,796 B1 | 12/2001 | Berube et al. |
| 6,364,876 B1 | 4/2002 | Erb et al. |
| 6,383,182 B1 | 5/2002 | Berube et al. |
| 6,398,781 B1 | 6/2002 | Goble et al. |
| 6,440,158 B1 | 8/2002 | Saab |
| 6,485,486 B1 | 11/2002 | Trembly et al. |
| 6,496,738 B2 | 12/2002 | Carr |
| 6,512,956 B2 | 1/2003 | Arndt et al. |
| 6,527,768 B2 | 3/2003 | Berube |
| 6,582,427 B1 | 6/2003 | Goble et al. |
| 6,592,579 B2 | 7/2003 | Arndt et al. |
| 6,675,050 B2 | 1/2004 | Arndt et al. |
| 6,706,040 B2 | 3/2004 | Mahon et al. |
| 6,823,218 B2 | 11/2004 | Berube |
| 6,878,147 B2 | 4/2005 | Prakash et al. |
| 6,905,510 B2 | 6/2005 | Saab |
| 6,957,108 B2 | 10/2005 | Turner et al. |
| 6,962,586 B2 | 11/2005 | Berube et al. |
| 7,101,369 B2 | 9/2006 | Van der Welde |
| 7,113,832 B2 | 9/2006 | Longo |
| 7,118,590 B1 | 10/2006 | Cronin |
| 7,128,739 B2 | 10/2006 | Prakash et al. |
| 7,147,632 B2 | 12/2006 | Prakash et al. |
| 7,180,307 B2 | 2/2007 | Wakino et al. |
| 7,244,254 B2 | 7/2007 | Brace et al. |
| 7,311,703 B2 | 12/2007 | Turovskiy et al. |
| 7,318,824 B2 | 1/2008 | Prakash et al. |
| 7,378,363 B2 | 5/2008 | Zheng et al. |
| 7,396,355 B2 | 7/2008 | Goldman et al. |
| 2002/0022836 A1 | 2/2002 | Goble et al. |
| 2003/0088242 A1* | 5/2003 | Prakash et al. ........... 606/33 |
| 2003/0153908 A1 | 8/2003 | Goble et al. |
| 2004/0254621 A1 | 12/2004 | Jones et al. |
| 2005/0015081 A1* | 1/2005 | Turovskiy et al. ........ 606/33 |
| 2005/0113893 A1 | 5/2005 | Saab |
| 2005/0149010 A1 | 7/2005 | Turovskiy et al. |
| 2005/0165389 A1 | 7/2005 | Swain et al. |
| 2006/0085054 A1 | 4/2006 | Zikorus et al. |
| 2006/0151485 A1 | 7/2006 | Cronin |
| 2006/0241576 A1 | 10/2006 | Diederich et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |
| 2006/0287649 A1 | 12/2006 | Ormsby et al. |
| 2006/0289528 A1 | 12/2006 | Chiu et al. |
| 2006/0293650 A1 | 12/2006 | Prakash et al. |
| 2006/0293651 A1 | 12/2006 | Cronin |
| 2006/0293652 A1 | 12/2006 | Van der Weide |
| 2007/0016181 A1 | 1/2007 | Van der Weide et al. |
| 2007/0043346 A1 | 2/2007 | Cronin |
| 2007/0049917 A1 | 3/2007 | Yang et al. |
| 2007/0060989 A1 | 3/2007 | Deem et al. |
| 2007/0185554 A1 | 8/2007 | Appling et al. |
| 2007/0203551 A1 | 8/2007 | Cronin et al. |
| 2007/0233057 A1 | 10/2007 | Konishi |
| 2007/0282319 A1 | 12/2007 | Van der Weide et al. |
| 2007/0288079 A1 | 12/2007 | Van der Weide et al. |
| 2009/0131926 A1* | 5/2009 | Rusin et al. ............... 606/33 |
| 2009/0248006 A1* | 10/2009 | Paulus et al. ............. 606/33 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946716 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 055 400 | 11/2000 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| GB | 2295094 | 5/1996 |
| GB | 2387544 | 10/2003 |
| GB | 2388039 | 11/2003 |
| GB | 2390545 | 1/2004 |
| GB | 2403148 | 12/2004 |
| GB | 2415630 | 1/2006 |

| | | |
|---|---|---|
| GB | 2416307 | 1/2006 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO 02/061880 | 8/2002 |
| WO | WO 03/024309 | 3/2003 |
| WO | WO 2005/011049 | 2/2005 |
| WO | WO 2007/024878 | 3/2007 |
| WO | WO 2007/076924 | 7/2007 |

OTHER PUBLICATIONS

International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report extended EP 09161502.1 dated Oct. 30, 2009.
European Search Report EP 09166708 dated Oct. 15, 2009.
International Search Report PCT/US98/18640 dated Jan. 29, 1998.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation-'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

European Search Report EP 98300964.8 dated Dec. 13, 2000.

European Search Report EP 98944778 dated Nov. 7, 2000.

European Search Report EP 98958575.7 dated Oct. 29, 2002.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol , vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non-LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.

U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 08/483,742, filed Jun. 7, 1995.
U.S. Appl. No. 08/136,098, filed Oct. 14, 1993.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
European Search Report EP 09161502.1 dated Jun. 10, 2010 (9 pages).

* cited by examiner

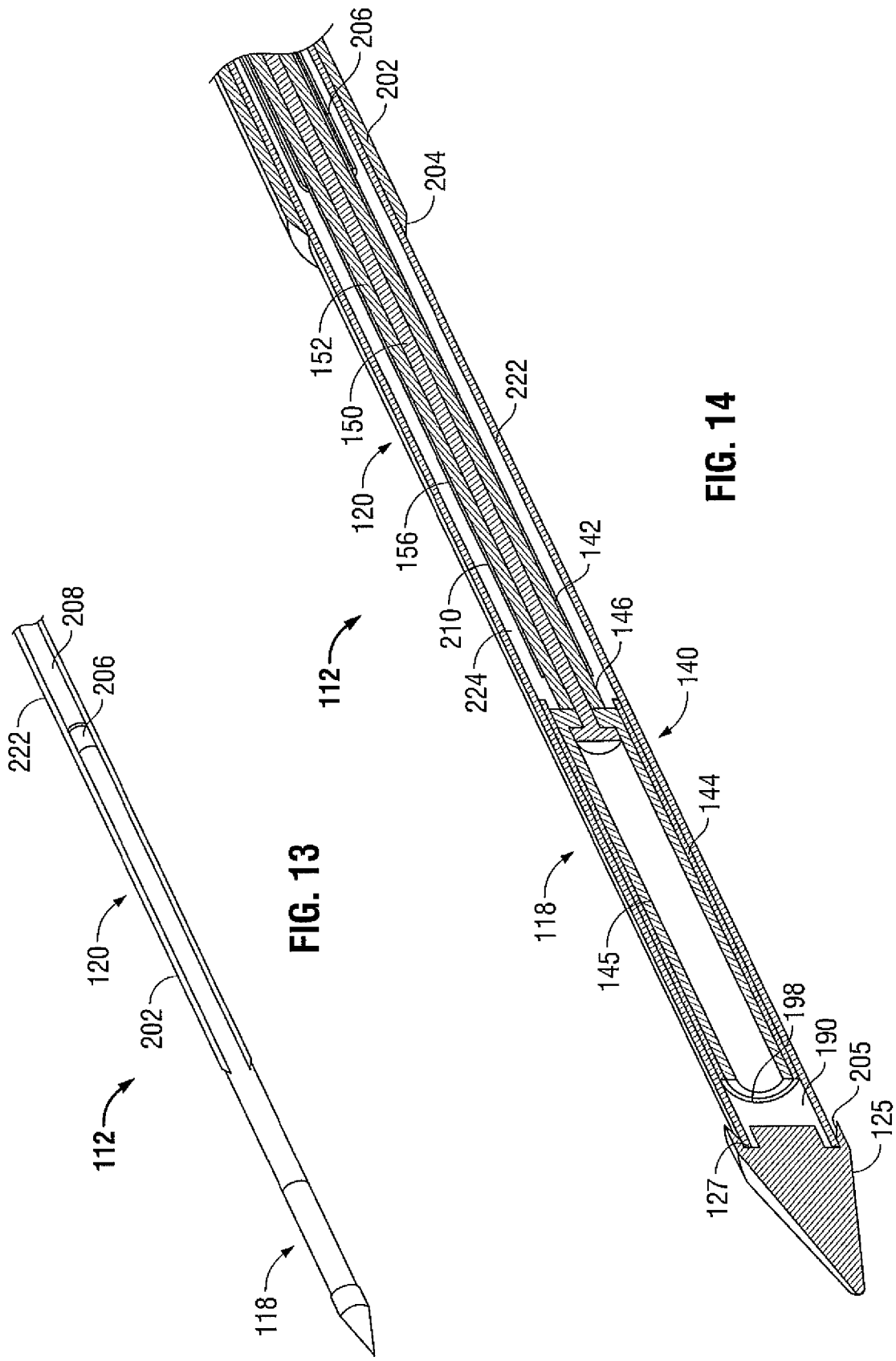

SLIDABLE CHOKE MICROWAVE ANTENNA

BACKGROUND

1. Technical Field

The present disclosure relates generally to microwave applicators used in tissue ablation procedures. More particularly, the present disclosure is directed to a microwave applicator having a slidable jacket that acts an electrical termination choke.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antenna assemblies that penetrate tissue to reach tumors. There are several types of microwave antennas, such as monopole and dipole. In monopole and dipole antennas, microwave energy radiates perpendicularly from the axis of the conductor. A monopole antenna includes a single, elongated microwave conductor. Dipole antennas may have a coaxial construction including an inner conductor and an outer conductor separated by a dielectric portion. More specifically, dipole microwave antennas are typically long, thin inner conductors that extend along a longitudinal axis of the antenna and are surrounded by an outer conductor. In certain variations, a portion or portions of the outer conductor may be selectively removed to enhance the outward radiation of energy. This type of microwave antenna construction is typically referred to as a "leaky waveguide" or "leaky coaxial" antenna.

Conventional microwave antennas tend to have a narrow operational bandwidth, a wavelength range at which optimal operational efficiency is achieved, and hence, are incapable of consistently maintaining a predetermined impedance match between the microwave delivery system (e.g., generator, cable, etc.) and the tissue surrounding the microwave antenna. More specifically, as microwave energy is applied to tissue, the dielectric constant of the tissue immediately surrounding the microwave antenna decreases as the tissue is treated. The drop causes the wavelength of the microwave energy being applied to tissue to increase beyond the bandwidth of the antenna. As a result, there is a mismatch between the bandwidth of conventional microwave antenna and the microwave energy being applied. Thus, narrow band microwave antennas tend to detune over use hindering the effective delivery and dispersion of energy.

Various improvements have been disclosed in the art, which aid in maintaining proper tuning of the antenna during use as the tissue is treated. However, these improvements tend to compromise the structural integrity of the antennas, requiring additional enhancement and/or instrumentation instruments to facilitate insertion of the antenna intro the target treatment area.

SUMMARY

According to one aspect of the present disclosure a microwave antenna assembly is disclosed. The antenna assembly includes a feedline having an inner conductor, an outer conductor and an inner insulator disposed therebetween and a radiating portion including a dipole antenna coupled to the feedline and a trocar coupled to the dipole antenna at a distal end thereof. The antenna assembly also includes a slidable outer jacket disposed about the radiating portion and the feedline. The slidable outer jacket being configured to slide about at least one of the radiating portion and the feedline from a closed configuration, in which the slidable outer jacket is mated with the trocar and a retracted configuration, in which the slidable outer jacket is retracted in a proximally exposing at least a portion the radiating portion.

According to another aspect of the present disclosure a microwave antenna assembly is disclosed. The antenna assembly includes a feedline having an inner conductor, an outer conductor and an inner insulator disposed therebetween and a radiating portion including a dipole antenna coupled to the feedline and a trocar coupled to the dipole antenna at a distal end thereof. The assembly also includes an inner fluid, which is disposed around the outer conductor in electromechanical contact therewith. The inner fluid feed member includes a plurality of fluid lumens defined therein configured to supply a fluid to the radiating portion. The assembly also includes an outer fluid feed member, which is disposed around the inner fluid feed member in electro-mechanical contact therewith. The outer fluid feed member also includes a plurality of fluid lumens defined therein configured to withdraw the fluid from the radiating portion.

A method for performing microwave ablation is also contemplated by the present disclosure. The method includes the step of providing a microwave antenna. The antenna assembly includes a feedline having all inner conductor, an outer conductor and an inner insulator disposed therebetween and a radiating portion including a dipole antenna coupled to the feedline and a trocar coupled to the dipole antenna at a distal end thereof. The antenna assembly also includes a slidable outer jacket disposed about the radiating portion and the feedline. The slidable outer jacket is configured to slide about at least one of the radiating portion and the feedline. The method also includes the steps of moving the slidable outer jacket into a closed configuration, in which the slidable outer jacket is mated with the trocar, inserting the microwave antenna into tissue and moving the slidable outer jacket into a retracted configuration, in which the slidable outer jacket is retracted proximally to expose at least a portion of the radiating portion.

BRIEF DESCRIPTION OF THE DRAWINGS

The above and other aspects, features, and advantages of the present disclosure will become more apparent in light of the following detailed description when taken in conjunction with the accompanying drawings in which:

FIG. 13 is a perspective, cross-sectional view of a microwave antenna assembly according to the present disclosure; and FIGS. 14-17 are enlarged, cross-sectional views of a portion of the microwave antenna assembly of FIG. 12.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
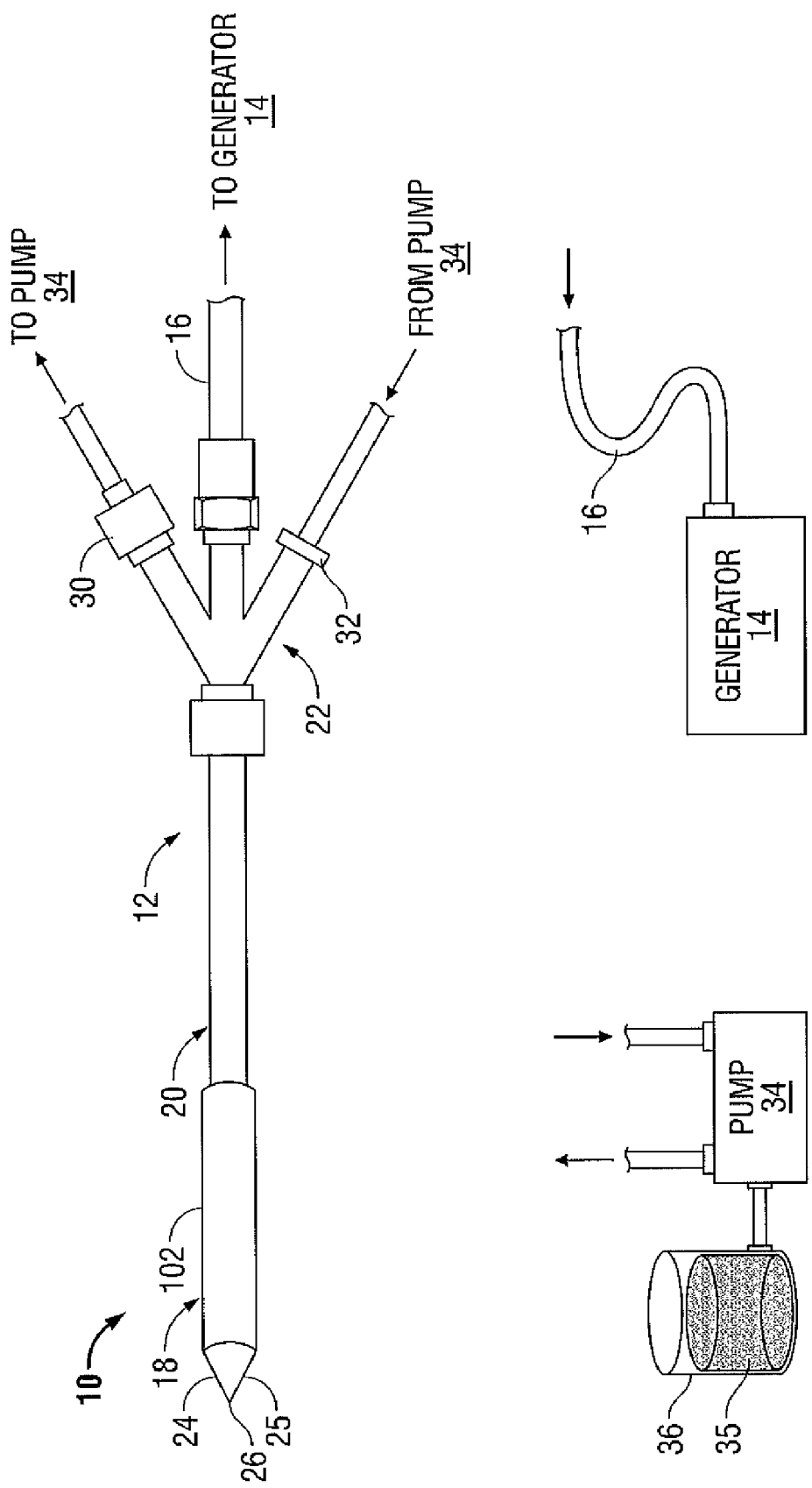
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. In one embodiment, the generator 14 is configured to provide microwave energy at an operational frequency from about 500 MHz to about 5000 MHz.

The antenna assembly 12 includes a radiating portion 18 that is connected by a feedline 20 (or shaft) to the cable 16. More specifically, the antenna assembly 12 is coupled to the cable 16 through a connection hub 22. The connection hub 22 also includes an outlet fluid port 30 and an inlet fluid port 32 defined therein that are in fluid communication with the radiating portion 18 and the feedline 20 allowing dielectric coolant fluid 35 from the ports 30 and 32 to be dispersed and circulated around the antenna assembly 12. The ports 30 and 32 are also coupled to a supply pump 34 that, in turn, is coupled to a supply tank 36 that stores the dielectric coolant fluid 35 and maintains the fluid at a predetermined temperature.

In one embodiment, the supply tank 36 may include a coolant unit (not shown), which cools the returning coolant fluid 35 from the antenna assembly 12. Alternatively, the coolant fluid may be a coolant gas.

Assembly 12 also includes a trocar 25 having tapered end 24 that terminates, in one embodiment, at a pointed tip 26 to facilitate insertion of the trocar into tissue with minimal resistance at a distal end of the radiating portion 18. In those cases where the radiating portion 18 is inserted into a pre-existing opening, tip 26 may be rounded or flat.

Figure 2:
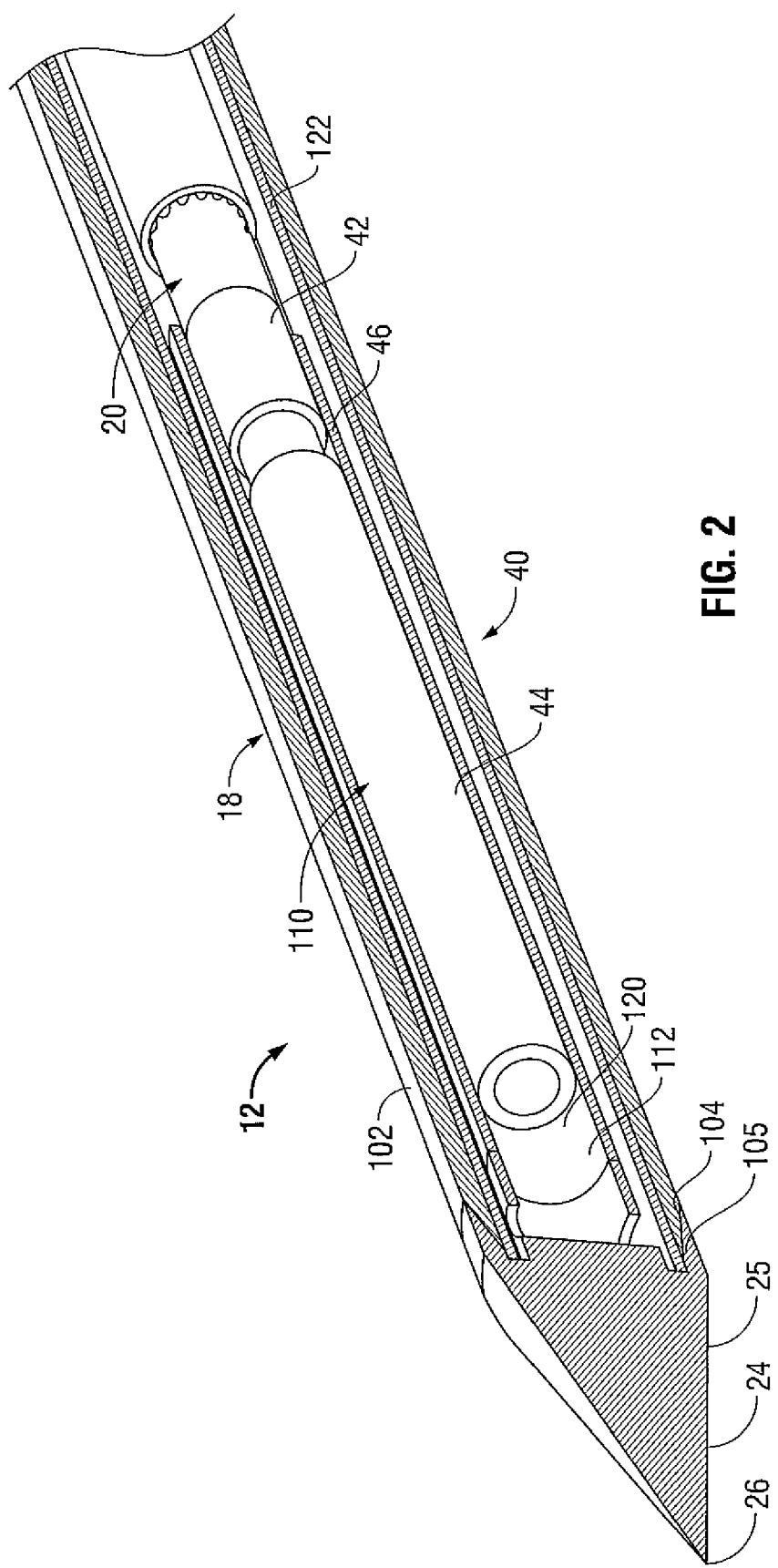
FIGS. 2 and 3 are perspective cross-sectional views of a microwave antenna assembly according to the present disclosure.
Figure 7:
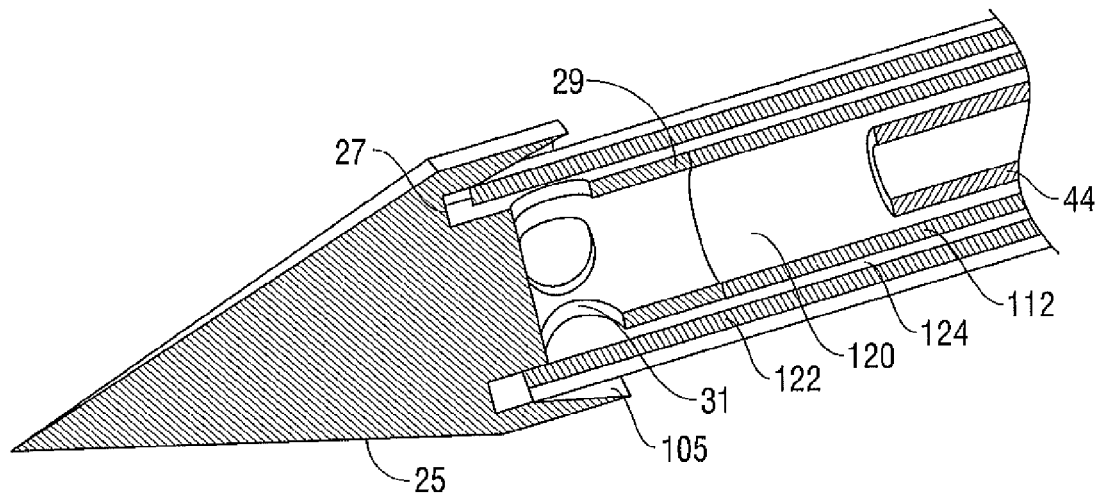
FIGS. 7-9 are enlarged, cross-sectional views of a trocar of the microwave antenna assembly of FIG. 2.
Figure 8:
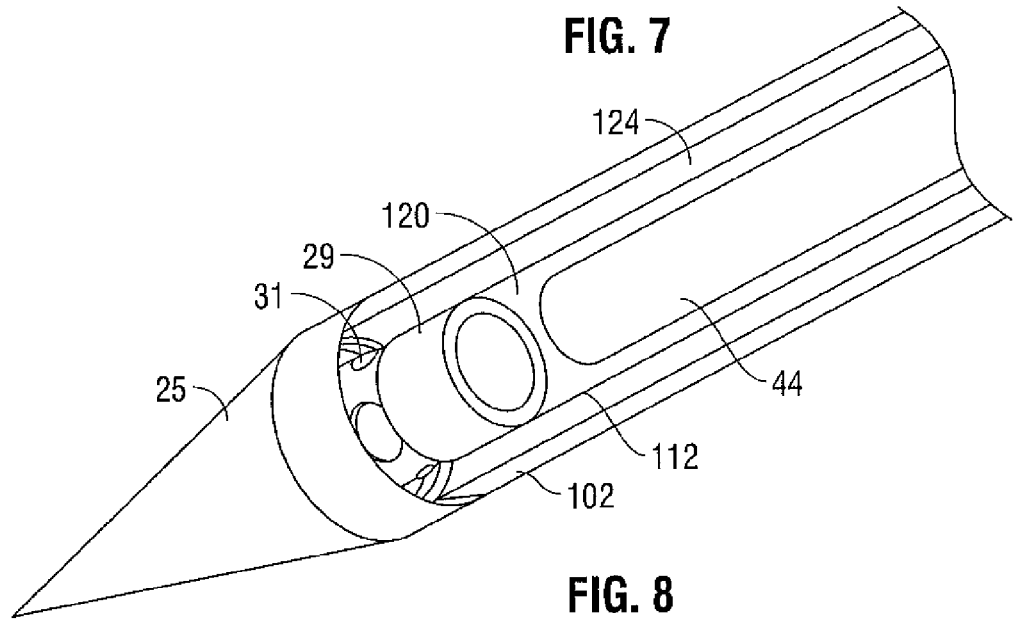

FIG. 2 illustrates the radiating portion 18 of the antenna assembly 12 having a slidable outer jacket 102. The radiating portion 18 has a substantially cylindrical shape and the outer jacket 102 has a substantially tubular shape defining an inner diameter substantially similar to the outer diameter of the radiating portion 18. More specifically, the outer jacket 102 is configured to slide along the radiating portion 18 between a closed configuration and a retracted configuration. In the closed configuration, the jacket 102 is disposed at the distal end of the assembly 12 and the distal end of the jacket 102 is positioned in contact with the trocar 25 as shown in FIG. 8. In the retracted configuration, the jacket 102 is slid proximally thereby exposing the radiating portion 18 as shown in FIG. 7.

The jacket 102 may be formed from any suitable type of conductive metal that has high tensile strength and does not react with tissue when inserted therein, such as stainless steel, titanium, and other types of suitable metals. With reference to FIG. 2, the distal end of the jacket 102 includes a tapered edge 104 configured to fit into a tapered rim 105 of the trocar 25. More specifically, the tapered rim 105 has substantially the same angle as the tapered edge 104 allowing the jacket 102 to mate with the trocar 25 when the jacket 102 is in the closed configuration as shown in FIG. 8.

Figure 3:
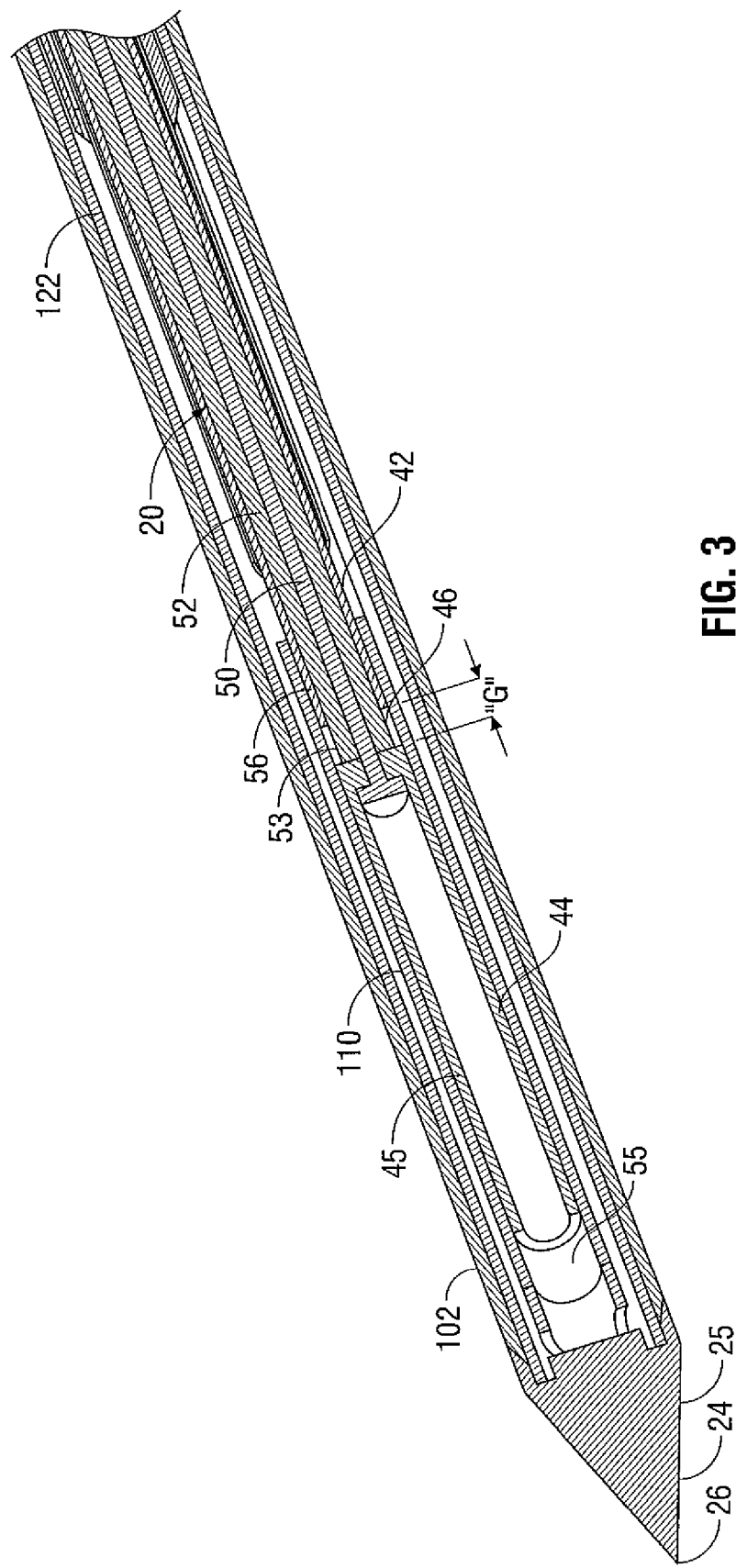

With reference to FIGS. 2 and 3, the radiating portion 18 includes a dipole antenna 40, which may be either balanced or unbalanced. The dipole antenna 40 is coupled to the feedline 20 that electrically connects antenna assembly 12 to the generator 14. As shown in FIG. 3, the feedline 20 includes an inner conductor 50 (e.g., a wire) surrounded by an inner insulator 52, which is then surrounded by an outer conductor 56 (e.g., a cylindrical conducting sheath). The inner and outer conductors 50 and 56 may be constructed of copper, gold, stainless steel or other conductive metals with similar conductivity properties. The metals may also be plated with other conductive materials, to improve the conductivity properties, e.g., to improve conductivity or decrease energy loss, etc. In one embodiment, the feedline 20 may be formed from a coaxial semi-rigid or flexible cable having a 0.047 inch outer diameter wire rated for 50 Ohms.

The dipole antenna 40 includes a proximal portion 42 and a distal portion 44 interconnected by a dielectric spacer (e.g., extended inner insulator 52) at a feed point 46. In one embodiment, where the antenna 40 is unbalanced, the distal portion 44 and the proximal portion 42 may be of different lengths. The proximal portion 42 is formed from the inner conductor 50 and the inner insulator 52, which are mutually extended outside the outer conductor 56, as shown best in FIG. 3. In one embodiment, in which the feedline 20 is formed from a coaxial cable, the outer conductor 56 and the inner insulator 52 may be exposed to reveal the inner conductor 50.

With continued reference to FIG. 3, the distal portion 44 includes a conductive member 45 that may be formed from any type of conductive material, such as a suitable metal (e.g., copper, stainless steel, tin, and various alloys thereof). The distal portion 44 may have a solid structure and may be formed from solid wire (e.g., 10 AWG). In another embodiment, the distal portion 44 may be formed from a hollow sleeve of an outer conductor of coaxial cable or another cylindrical conductor. The cylindrical conductor may then be filled with solder to convert the cylinder into a solid shaft or the cylinder may be left hollow. More specifically, the solder may be heated to a temperature sufficient to liquefy the solder within the cylindrical conductor (e.g., 500° F.), thereby creating a solid shaft.

In another embodiment, the proximal portion 42 may also be formed from solid wire or a cylindrical conductor filled with solder. The proximal portion 42 is thereafter coupled to the inner conductor 50. This may be accomplished by soldering the proximal portion 42 to the distal end of the inner conductor 50, such as by melting the solder of the proximal portion 42 and inserting the inner conductor 50 therein.

The distal portion 44 may be soldered to the inner conductor 50 of the proximal portion 42 to establish electromechanical contact therebetween. In one embodiment, where the distal portion 44 is formed from a hollow cylindrical conductor filled with a solder material, the distal portion 44 may be attached to the proximal portion 42 by liquefying the solder of the distal portion 44 and inserting the distal end of the inner conductor 50 therein. A portion of the distal end of the inner conductor 50 is inserted into the distal portion 44 such that a dipole feed gap "G" remains between the proximal and distal portions 42 and 44 as shown in FIG. 3. The gap "G" may be from about 1 mm to about 3 mm. The dipole feed gap "G" of the antenna is the first structure the coaxial field mode encounters upon transfer to free space. In one embodiment, the gap "G" is thereafter filled with a dielectric material to form the dielectric spacer at the feed point 46. The dielectric material may be polytetrafluoroethylene (PTFE), such as Teflon® sold by DuPont of Willmington, Del. In another embodiment, the gap "G" may be coated via a dielectric seal coating as discussed in more detail below.

Since the radiating portion 18 and the feedline 20 are directly in contact with a coolant fluid, these components of the assembly 12 must be sealed to prevent fluid seepage via a cast seal 110. This may be accomplished by applying any type of melt-processible polymers using conventional injection molding and screw extrusion techniques to form a cast seal 110 around the radiating portion 18 and the feedline 20 (See FIG. 2). The cast seal 110 may be formed from any suitable heat resistant and chemically inert polymer material such as fluorinated ethylene propylene (FEP) or polytetrafluoroethylene (PTFE), such as Teflon® sold by DuPont of Willmington, Del. In another embodiment, other suitable materials, which include silicone, epoxies, and casting resins may also be used.

In one embodiment, the cast seal 110 may be applied as shrink wrap. The polymer may be applied to the entire assembly 12, namely the feedline 20 and the radiating portion 18. The shrink wrap is then heated to seal the feedline 20 and radiating portion 18. The resulting cast seal 110 prevents any coolant fluid from penetrating into the assembly 12. In addition, the cast seal 110 is also applied at the point where the inner conductor 50 and the inner insulator 52 are extended past the outer conductor 56, thereby creating a space 53 at the feed point 46 and a space 55 between the trocar 25 and the distal portion 44 as shown in FIG. 3.

Figure 4:
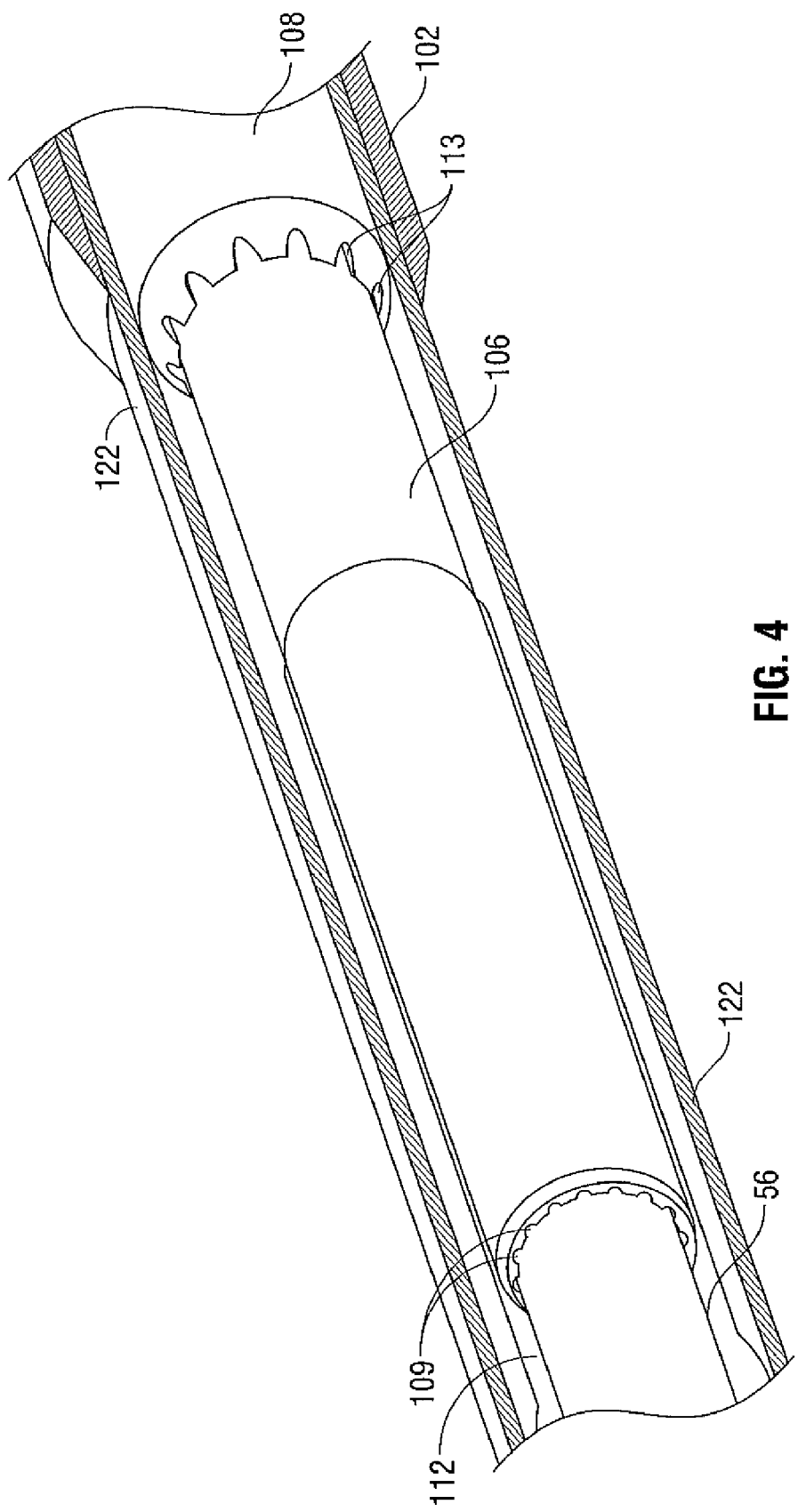
FIG. 4 is an enlarged, cross-sectional view of a portion of the microwave antenna assembly of FIG. 2.
Figure 5:
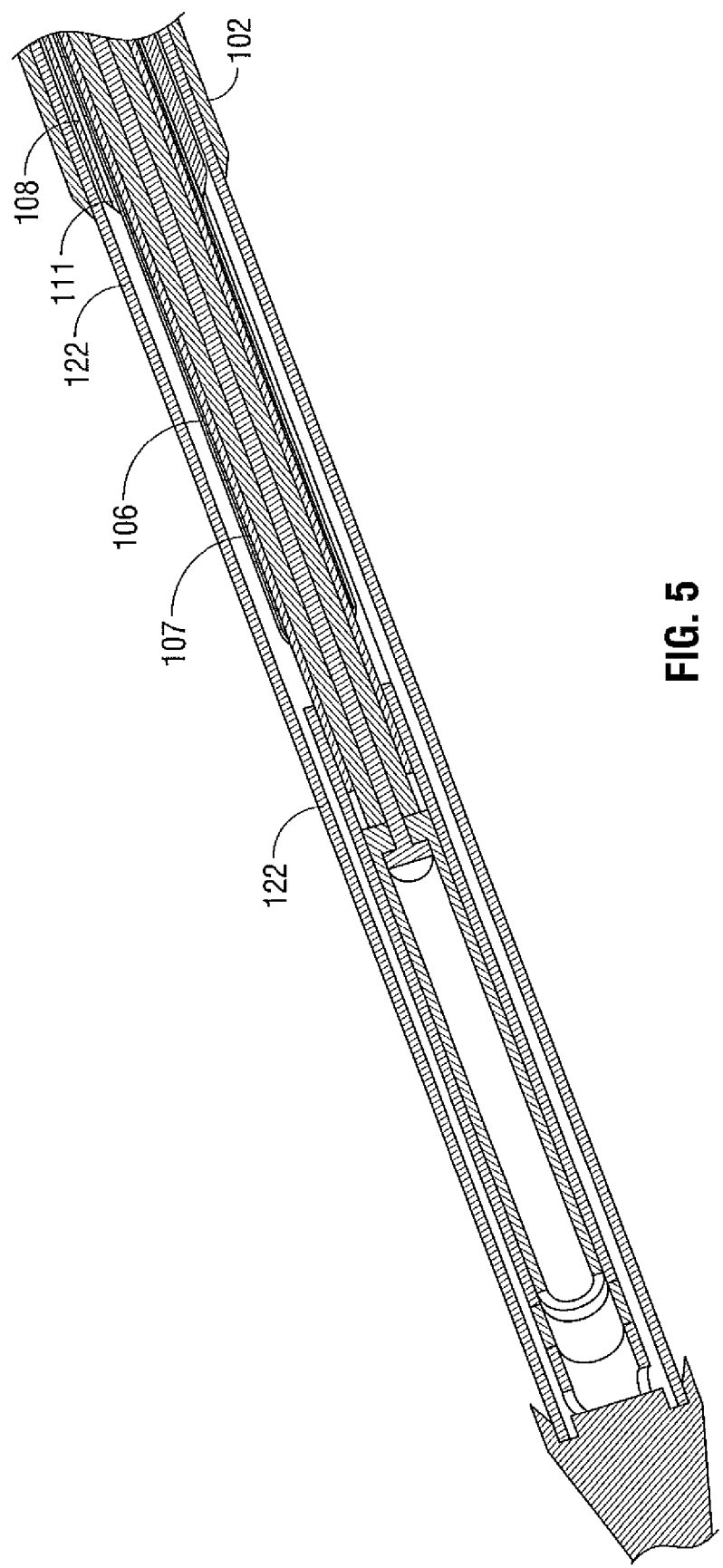
FIG. 5 is a perspective, cross-sectional view of a microwave antenna assembly of FIG. 2.
Figure 6:
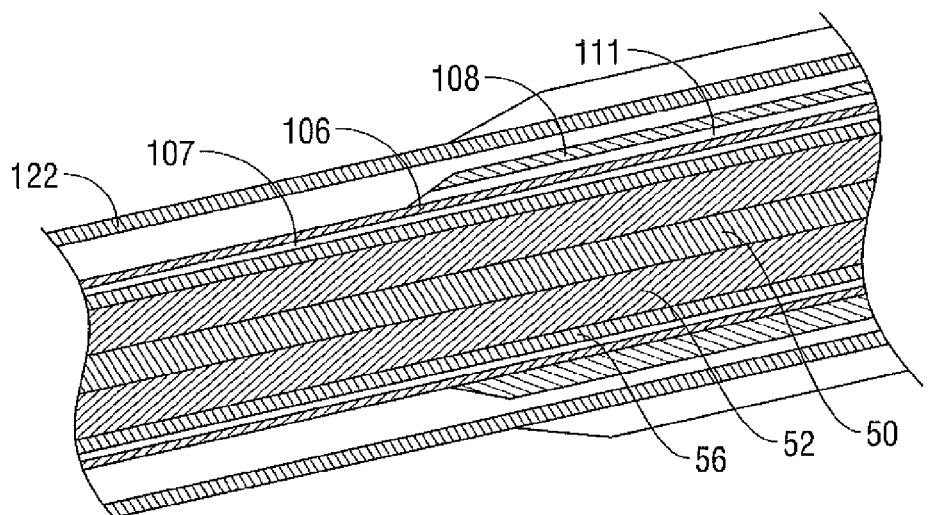
FIG. 6 is an enlarged, cross-sectional view of a portion of the microwave antenna assembly of FIG. 2.

With reference to FIGS. 4-6, the assembly includes an inner fluid feed member 106 and an outer fluid feed member 108, The fluid feed members 106 and 108 have a substantially tubular shape and are formed from a conductive metal, such as copper, stainless steel, tin, and various alloys thereof. In another embodiment, the fluid feed members 106 and 108 may also be formed from other types of microwave impermeable materials, which may be dielectric materials having an outer surface thereof coated with a conductive material (e.g., metal). The conductive material coating has a thickness sufficient to prevent current leakage. More specifically, the thickness of the coating depends on the maximum skin penetration depth for the metal used in the coating at a predetermined microwave frequency.

The fluid feed member 106 is disposed around the outer conductor 56 and is in electro-mechanical contact therewith. In addition, the fluid feed member 106 extends from any point past the outer conductor 56 along the length thereof to the proximal end of the feedline 20 where the fluid feed member 106 is coupled to the connection hub 22 and is in fluid communication therewith.

The fluid feed member 106 includes one or more fluid lumens 107 defined therein as shown in FIGS. 5 and 6. The fluid lumens 107 terminate in one or more openings 109 defined at the distal end of the fluid feed member 106. If a plurality of openings 109 is included, a grille-type structure may be included at the distal end of the fluid feed member 106. The fluid lumens 107 may be drilled in the tubular structure of the fluid feed member 106. Alternatively, the fluid lumens 107 may be formed during casting of the fluid feed member 106. A plurality of openings 109 allows for lumen of coolant fluid and, in addition, minimizes and/or prevents microwave energy escaping or dissipating back up along the outer surface of the feedline 20.

The fluid feed member 108 is disposed around the fluid feed member 106 and is in electro-mechanical contact therewith. Thus, there is electrical contact continuity between the outer conductor 56 and the fluid feed members 106 and 108. The fluid feed member 108 also includes one or more fluid lumens 111 formed therein which also terminate in one or more respective openings 113 as shown in FIGS. 5 and 6.

With reference now to FIGS. 7-8, the trocar 25 has a generally conical shape and includes a base portion 27 as the base of the conical shape with the tapered rim 105 extending outward from the base portion 27 in the proximal direction. The trocar 25 also includes a tubular portion 29 disposed centrally on the base portion 27. The tubular portion 29 includes one or more openings 31 that provide for continuous fluid flow at the distal end of the radiating portion 18 as discussed in more detail below.

The trocar 25 may be formed from a variety of heat-resistant materials suitable for penetrating tissue, such as metals (e.g., stainless steel) and various thermoplastic materials, such as poletherimide, polyamide thermoplastic resins, an example of which is Ultem® sold by General Electric Co. of Fairfield, Conn. The trocar 25 may be machined from various stock rods to obtain a desired shape.

The trocar 25 is coupled to the radiating portion 18 of the antenna 40 by an inner cooling jacket 112. As shown in FIGS. 2 and 7, the cooling jacket 112 is disposed on top of the fluid feed member 106 and extends therefrom the length of the antenna 40 to the distal end of the radiating portion 18 where the cooling jacket 112 is coupled to the tubular portion 29 of the trocar 25. At least a portion of the cooling jacket 112 has an inner diameter that is larger than the outer diameter of antenna 40 thereby defining a first tubular fluid lumen 120 around the antenna 40. The cooling jacket 112 is coupled to the fluid feed member 106 to create a waterproof seal around the outer surface thereof.

A suitable material for the cooling jacket 112 has a minimal dielectric constant so that the material does not affect the electrical performance of the assembly 12 and is capable of withstanding temperatures generated during ablation at the radiating portion 18. In addition, the material is suitable to withstand fluid pressure due to the coolant supplied into the fluid lumen 120. In one embodiment, a sleeve of any suitable heat resistant polymer material, such as fluorinated ethylene propylene (FEP) or polytetrafluoroethylene (PTFE), such as Teflon® sold by DuPont of Willmington, Del. may be used. Additional adhesive may be used to attach the polymer material to the fluid feed member 106 and the tubular portion 27.

An outer cooling jacket 122 is also included in the assembly 12 as shown in FIGS. 2-7. The cooling jacket 122 is disposed around the fluid feed member 108 to form a waterproof seal thereabout and extends to the trocar 25. More specifically, the cooling jacket 122 is coupled to one of the base portion 27 or the tapered rim 105 of the trocar 25 such that there is sufficient clearance for the outer jacket 102 to mate with the trocar 25. Since the cooling jacket 122 is disposed on top of the fluid feed member 108, which has an outer diameter larger than the fluid feed member 106, the cooling jacket 122 defines a second tubular fluid lumen 124 around the cooling jacket 112. The cooling jacket 122 may be formed from similar materials as the cooling jacket 112. In one embodiment, the cooling jacket 122 may be any type of rigid tubing such as a catheter manufactured from polyimide and other types of polymers.

Figure 9:
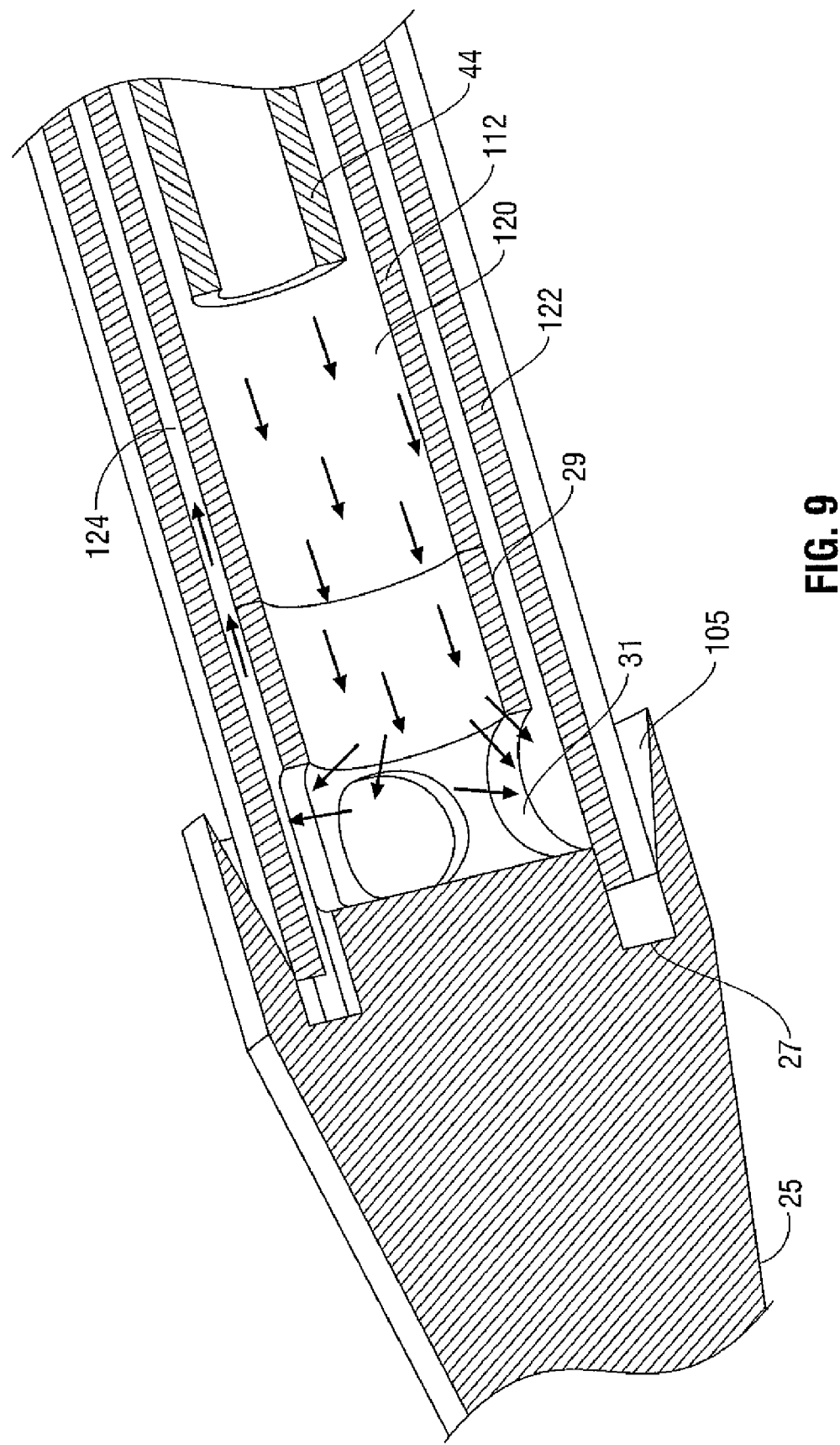

During operation, the dielectric coolant fluid 35 (e.g., saline, deionized water, etc.) is supplied to the assembly 12 by the pump 34 through the connection hub 22, which is in fluid communication with the fluid feed members 106 and 108. The fluid 35 enters the radiating portion 18 through the feed member 106 and flows into the first fluid lumen 120, along the inner surface of the cooling jacket 112, thereby contacting the antenna 40 and removing heat. Since the antenna 40 is sealed by the cast seal 110 the fluid comes directly into physical contact with antenna 40. As the fluid continues down the fluid lumen 120 the fluid enters the tubular portion 29 of the trocar 25. As shown in FIG. 9, the fluid 35 flows through the openings 31 which interconnect the first and second fluid lumens 120 and 124. The second fluid lumen 124 thereby serves as a flow return path into the fluid flow line 108, which is coupled to the outlet fluid port 30.

In another embodiment, the fluid flow may be reversed, and the fluid may be supplied through the fluid flow line 108 such that the fluid flows through the second fluid lumen 124 and enters into the first fluid lumen 120 through the trocar 25. The fluid 35 is then suctioned out through the fluid flow line 106. In this configuration, the fluid 35 comes in contact with the antenna 40 along the flow return path.

The above-discussed coolant system provides for circulation of dielectric coolant fluid 35 (e.g., saline, deionized water, etc.) through the entire length of the antenna assembly 12. The dielectric coolant fluid 35 removes the heat generated by the assembly 12. In addition, the dielectric coolant fluid 35 acts as a buffer for the assembly 12 and prevents near field dielectric properties of the assembly 12 from changing due to varying tissue dielectric properties. As microwave energy is applied during ablation, desiccation of the tissue around the radiating portion 18 results in a drop in tissue complex permittivity by a considerable factor (e.g., a factor of about 10). This dielectric constant (er') drop increases the wavelength of microwave energy in the tissue, which dramatically affects the impedance of un-buffered microwave antenna assemblies, thereby mismatching the antenna assemblies from the system impedance (e.g., impedance of the cable 16 and the generator 14). The increase in wavelength also results in a power dissipation zone that is much longer in length along the assembly 12 than in cross sectional diameter. The decrease in tissue conductivity (er") also affects the real part of the impedance of the assembly 12. The fluid dielectric buffering of the present disclosure moderates the increase in wavelength of the delivered energy and drop in conductivity of the near field, thereby reducing the change in impedance of the assembly 12. This allows for a more consistent antenna-to-system impedance match and spherical power dissipation zone despite tissue behavior.

The buffering of wavelength variation also allows for a more effective choking network. Choking is placed at a current point, or high impedance point, on the end of the proximal portion 42. With wavelength buffering in the choked wet tip, the half wavelength current pattern on the dipole radiating section is maintained, making the position of the high impedance point less variable and therefore allowing for a more effective choke network. Together, the cable cooling and the dielectric buffering allow for targeted and efficient energy delivery to the tissue to enable nearly spherical ablation zones and fast ablation times. Either saline or deionized water can be used with the assembly 12.

The slidable outer jacket 102 also provides a dual purpose. In closed configuration, the jacket 102 acts as a protective cover for the radiating portion 18. In addition, the outer jacket 102 increases the structural integrity of the assembly 12 during insertion. When the jacket 102 is in retracted configuration, the jacket 102 acts as a choke. The jacket 102 is typically disposed in the closed configuration during insertion of the assembly 12 into tissue and is slid back to expose the radiating section 18 once we target tissue is reached. Microwave energy and coolant 35 are thereafter supplied through the assembly 12 to perform the desired treatment procedure.

In the retracted configuration illustrated in FIGS. 4 and 5, the jacket 102 is slid back to a distance substantially equal to half the operating wavelength. The retractable distance of the jacket 102 may be controlled by providing corresponding lock and grooves (not explicitly shown) on the mating surfaces of the jacket 102 and the fluid feed member 108 or other types of tactile feedback or suitable indicators. The grooves guide the sliding of the jacket 102 and prevent further proximal movement thereof once the jacket 102 is fully retracted. In another embodiment, the jacket 102 may be slid to any desirable length (e.g., quarter wave).

The jacket 102 is disposed on top of at least a portion of the fluid feed member 108. More specifically, the jacket 102 is shorted (e.g., in electro-mechanical contact with) to the outer conductor 56 of the feedline 20 via a contact assembly 130 and the fluid feed members 106 and 108, which provide electrical continuity therebetween. This configuration allows the jacket 102 to act as a half wavelength choke when the jacket 102 is in the retracted configuration. In this configuration, the jacket 102 confines the microwave energy from the generator 14 to the radiating portion 18 of the assembly 12 thereby limiting the microwave energy deposition zone length along the feedline 20. Namely, a shorted choke placed at the high impedance point of the proximal portion 42 on the dipole confines antenna currents to the radiating section 18 and reduces the length while maximizing the cross sectional diameter of ablations due to nearly spherical power dissipation zones. To aid the sliding of the jacket 102, the outer surface of the fluid feed member 108 may be coated by a friction reducing material.

With reference to FIGS. 10A-11B, the assembly 12 includes a contact assembly 130 disposed on the proximal portion of the fluid feed member 108. The contact assembly 130 is disposed at a location at which the jacket 102 is always in contact therewith, e.g., the jacket 102 is continually in contact with the contact assembly 130 in either closed or retracted configuration. The contact assembly 130 includes a tubular housing 132 having stop members 134 disposed at the proximal and distal ends thereof. The tubular housing 132 is formed from a conductive metal and is disposed about the fluid feed member 108. The contact assembly 130 further includes a spring member 136 disposed between the stop members 134. The spring member 136 may also be formed from a conductive tensile material suitable for coiling, which is coupled to tubular housing 132 at either one of the ends thereof.

Figure 11A:
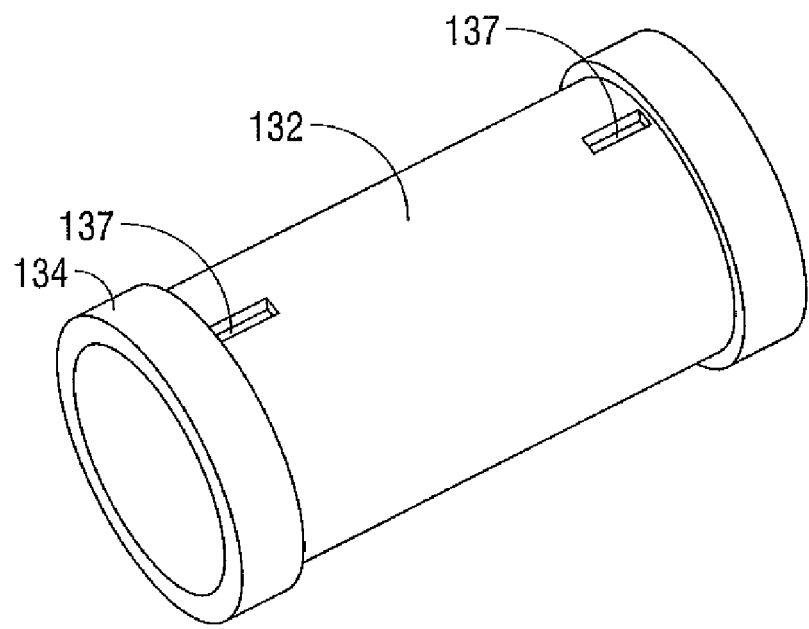
FIGS. 11A-B are perspective views of the contact assembly of FIGS. 10A-B.
Figure 11B:
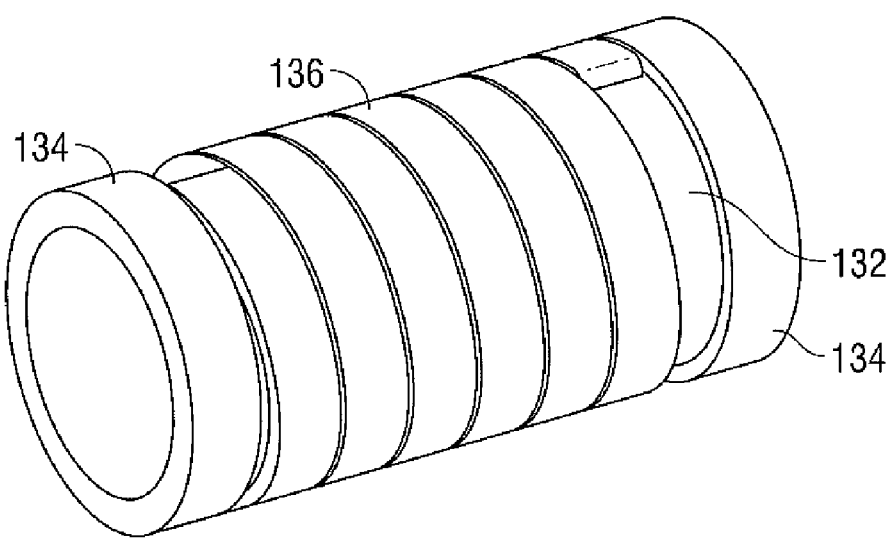

As shown in FIG. 11A, the tubular housing 132 may include one or more grooves 137 in the outer surface thereof. The ends of the spring member 136 may be bent and inserted into the grooves 137, which in combination with the stop members 134 prevent torsional and longitudinal displacement of the spring member 136 as shown in FIG. 11B.

As the jacket 102 is slid across the fluid feed member 108, the spring member 136 is pushed outwards due to mechanical forces and contacts the inner surface of the jacket 102 thereby maintaining an electrical connection between the outer conductor 56 and the jacket 102. In one embodiment, the spring member 136 may be coated by a conductive and/or corrosion resistant coating to facilitate sliding the jacket 102 and maintaining electrical contact therebetween. The coating may include various metal compounds such nickel, silver, and the like.

Figure 12:
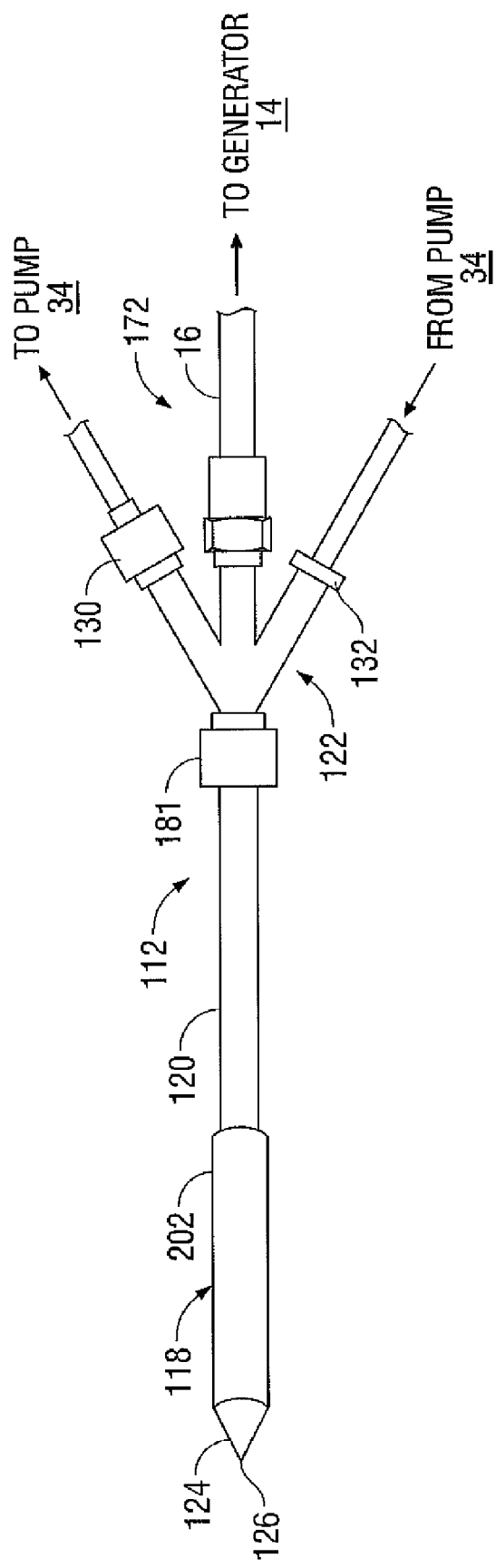
FIG. 12 is a schematic diagram of a microwave ablation system according one embodiment of the present disclosure.

FIGS. 12-14 illustrate another embodiment of a microwave antenna assembly 112 having a radiating portion 118 and a feedline 120 that couples the assembly 112 to the cable 16. More specifically, the antenna assembly 112 is coupled to the cable 16 through a connection hub 122 that includes an outlet fluid port 130 and an inlet fluid port 132 defined therein. The assembly 112 includes a slidable outer jacket 202 configured to slide between a closed configuration and a retracted configuration. The assembly 112 further includes a trocar 125 disposed at the distal end thereof. The trocar 125 includes a tapered rim 205 that is adapted to mate with a tapered edge 204 of the jacket 202 when the jacket 202 is in closed configuration. The assembly 112 also includes the connection hub 122 having a cable connector and fluid ports 130 and 132. The cable connector 179 is coupled to the inner conductor 152 and outer conductor 156 extendes outside the outer conductor 156 at the proximal end of the feedline 120.

FIGS. 13 and 14 illustrate the radiating portion 118 of the antenna assembly 112 having a dipole antenna 140 that is enclosed by a solid dielectric loading 190. The dipole antenna 140 may be either balanced or unbalanced. The dipole antenna 140 is coupled to the feedline 120, which electrically connects antenna assembly 112 to the generator 14. As shown in FIG. 14, similar to the feedline 20, the feedline 120 includes an inner conductor 150 (e.g., wire) surrounded by an inner insulator 152 which is then surrounded by an outer conductor 156 (e.g., cylindrical conducting cooling jacket).

The dipole antenna 140 includes a proximal portion 142 and a distal portion 144 that includes a conductive member 145. The distal and proximal portions are interconnected by a dielectric spacer at a feed point 146. The proximal portion 142 is formed from the inner conductor 150 and the inner insulator 152 that are extended outside the outer conductor 156. In one embodiment, in which the feedline 120 is formed from a coaxial cable, the outer conductor 156 and the inner insulator 152 may be exposed to reveal the inner conductor 150 as shown in FIG. 14.

The distal portion 144 may be formed from any type of conductive material, such as metals (e.g., copper, stainless steel, tin, and various alloys thereof. The portion 144 may have a solid structure and may be formed from solid wire (e.g., 10 AWG) or a cylindrical conductor filled with solder similar to the portion 44 of the assembly 12. The proximal portion 144 is thereafter coupled to the inner conductor 150.

The assembly 112 includes a solid dielectric loading 190 disposed over the dipole antenna 140. The loading 190 is also coupled to the trocar 125. The loading 190 may be cylinder-shaped having a central cavity 198 defined therein suitable for insertion over the distal portion 144 of the antenna 140. The cavity 198 may have a substantially cylindrical shape suitable to fit over the antenna 140 depending on the cross-sectional shape thereof. The dielectric loading 190 is coupled to the trocar 125 at the distal end of the assembly 112.

In one embodiment, the dielectric material of the loading 190 may have a dielectric constant of from about 2.5 and 150 and may be made from a ceramic material, such as alumina ceramic or a plastic material, such as a polyamide plastic (e.g., VESPEL® available from DuPont of Wilmington, Del.). The loading 190 acts as a dielectric buffer between the radiating portion 118 and the tissue so that as the electrical properties of the tissue change during ablation the antenna assembly 112 remains halfwave resonant and impedance-matched to the energy delivery system (e.g., the generator 14, the cable 16, etc.) throughout the ablation procedure.

Figure 15:
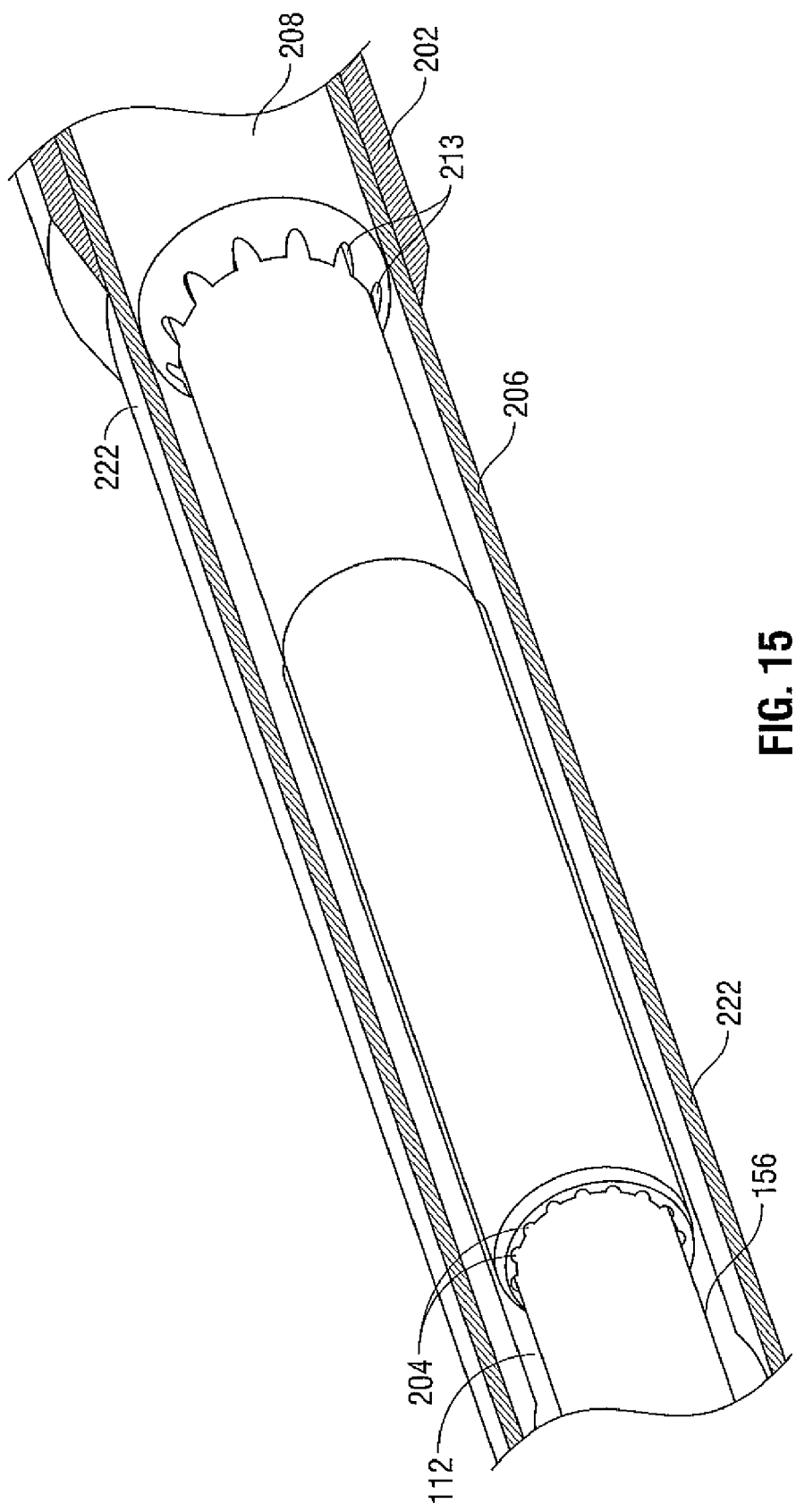
Figure 16:
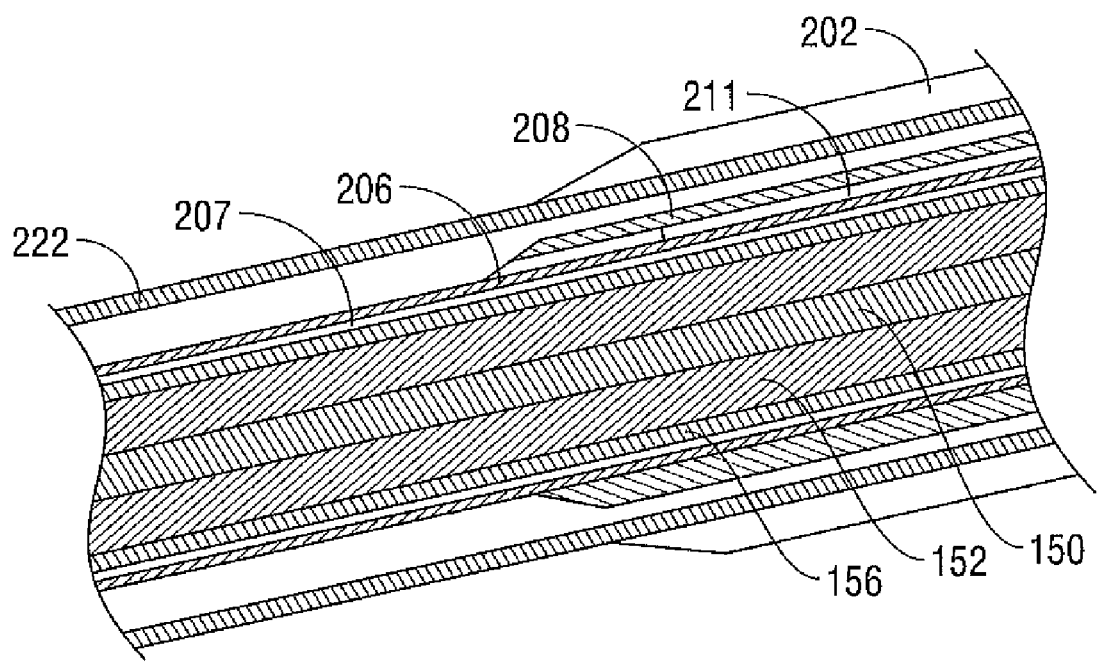
Figure 17:
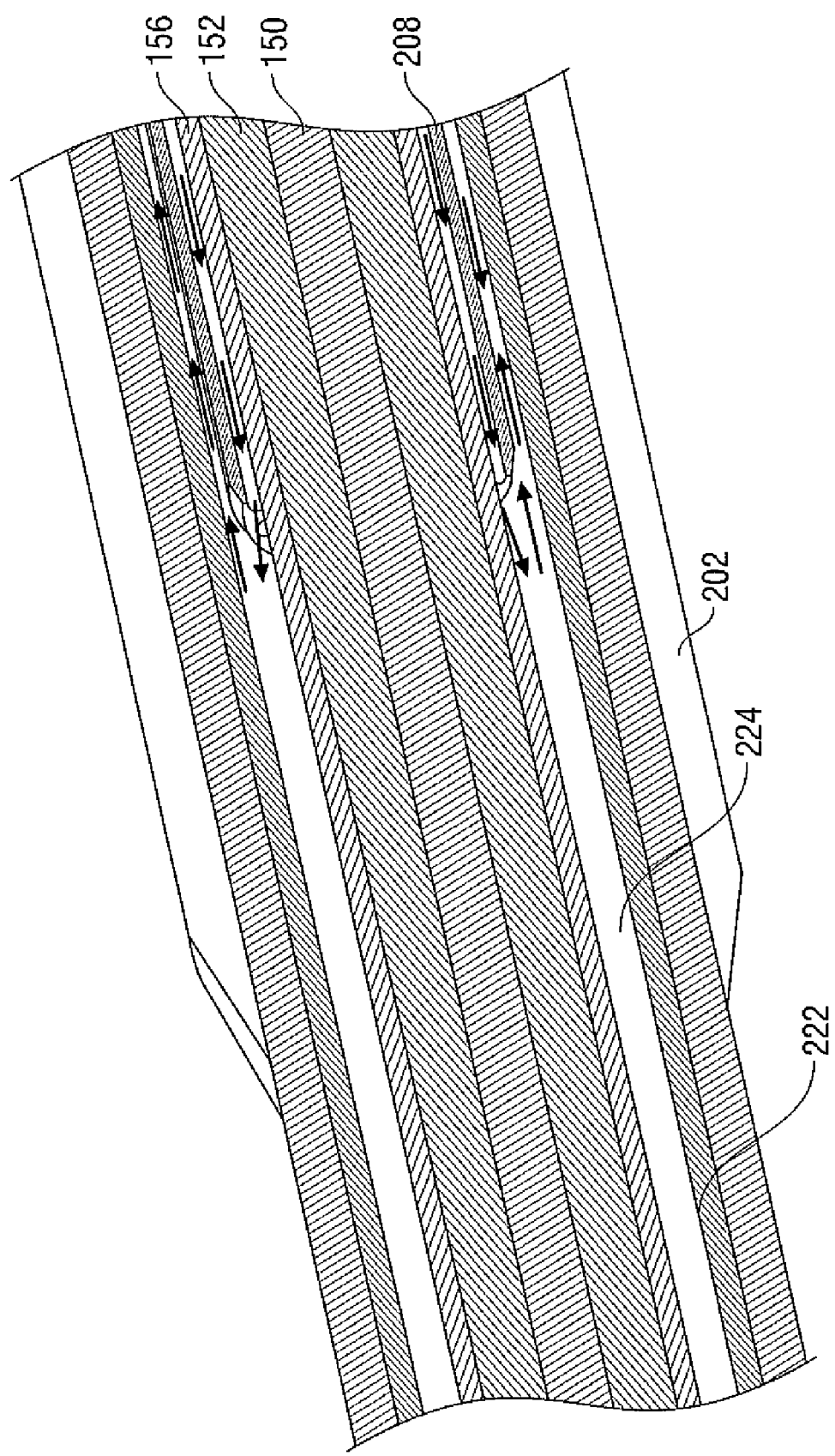

Since the feedline 120 is in contact with the coolant fluid 35, the feedline 120 is sealed to prevent any fluid seeping thereinto via a cast seal 210 similar to the cast seal 110. The assembly 112 also includes an inner fluid feed member 206 and an outer fluid feed member 208 as shown in FIGS. 14-16. The fluid feed members 206 and 208 have a substantially tubular shape and are formed from a conductive metal, such as copper, stainless steel, tin, and various alloys thereof or may be coated with a conductive material (e.g., metal). The fluid feed members 206 and 208 are coupled to the connection hub 122 and are configured to circulate fluid through the assembly 112. The fluid feed members 206 and 208 includes one or more fluid lumens 207 and 211, respectively, defined therein which terminate in one or more openings defined in the distal end thereof similar to the fluid feed members 106 and 108. The fluid feed member 206 is disposed around the outer conductor 156 and is in electro-mechanical contact therewith. The fluid feed member 208 is, in turn, disposed about the fluid feed member 208 with the distal end thereof terminating proximally of the distal end of the fluid feed member 206.

An outer cooling jacket 222 is included in the assembly 12 as shown in FIG. 14. The cooling jacket 222 is disposed around the fluid feed member 208 to form a waterproof seal thereabout and extends to the trocar 125, thereby enclosing the loading 190. More specifically, the cooling jacket 122 is coupled the base portion 127 or the tapered rim 205 of the trocar 125 such that there is sufficient clearance for the outer jacket 202 to mate with the trocar 125. Since the cooling jacket 222 is disposed on top of the fluid feed member 208, the cooling jacket 222 defines a fluid lumen 224 around feedline 120. The cooling jacket 222 extends to the trocar 125 and may be formed from similar materials as the cooling jackets of assembly 12.

During operation, the dielectric coolant fluid 35 (e.g., saline, deionized water, etc.) is supplied to the assembly 112 by the pump 34 through the connection hub 122, which is in fluid communication with the fluid feed members 206 and 208. Similar to the system described above, the fluid 35 flows into the fluid lumen 224 from the fluid feed member 206 thereby contacting the outer conductor 156 and removing heat. Since the outer conductor 156 is sealed by the cast seal 210, the coolant fluid 35 is not in direct physical contact therewith. The fluid 35 is withdrawn through the fluid feed member 208, thereby circulating the fluid 35 from the distal end to the proximal end of the feedline 120. In another embodiment, the fluid 35 flow may be reversed, and the fluid 35 may be supplied through the fluid flow line 208 such that the fluid flows and then suctioned out through the fluid flow line 206.

Figure 10A:
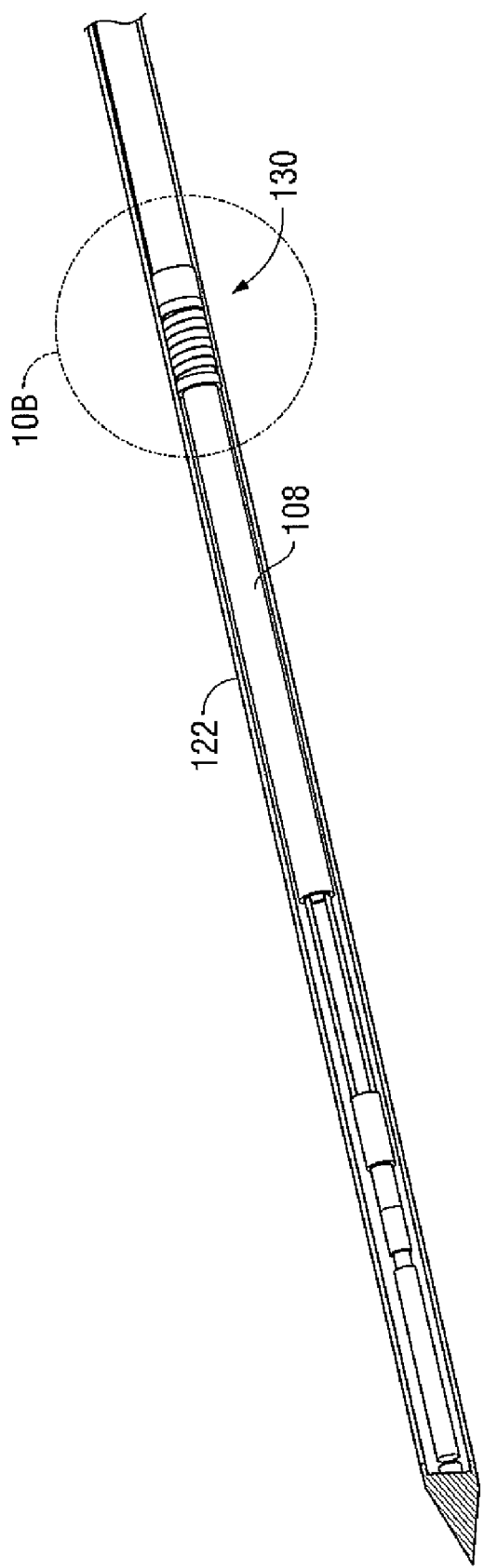
FIGS. 10A-B are perspective, cross-sectional views of a contact assembly of the microwave antenna assembly of FIG. 2.
Figure 10B:
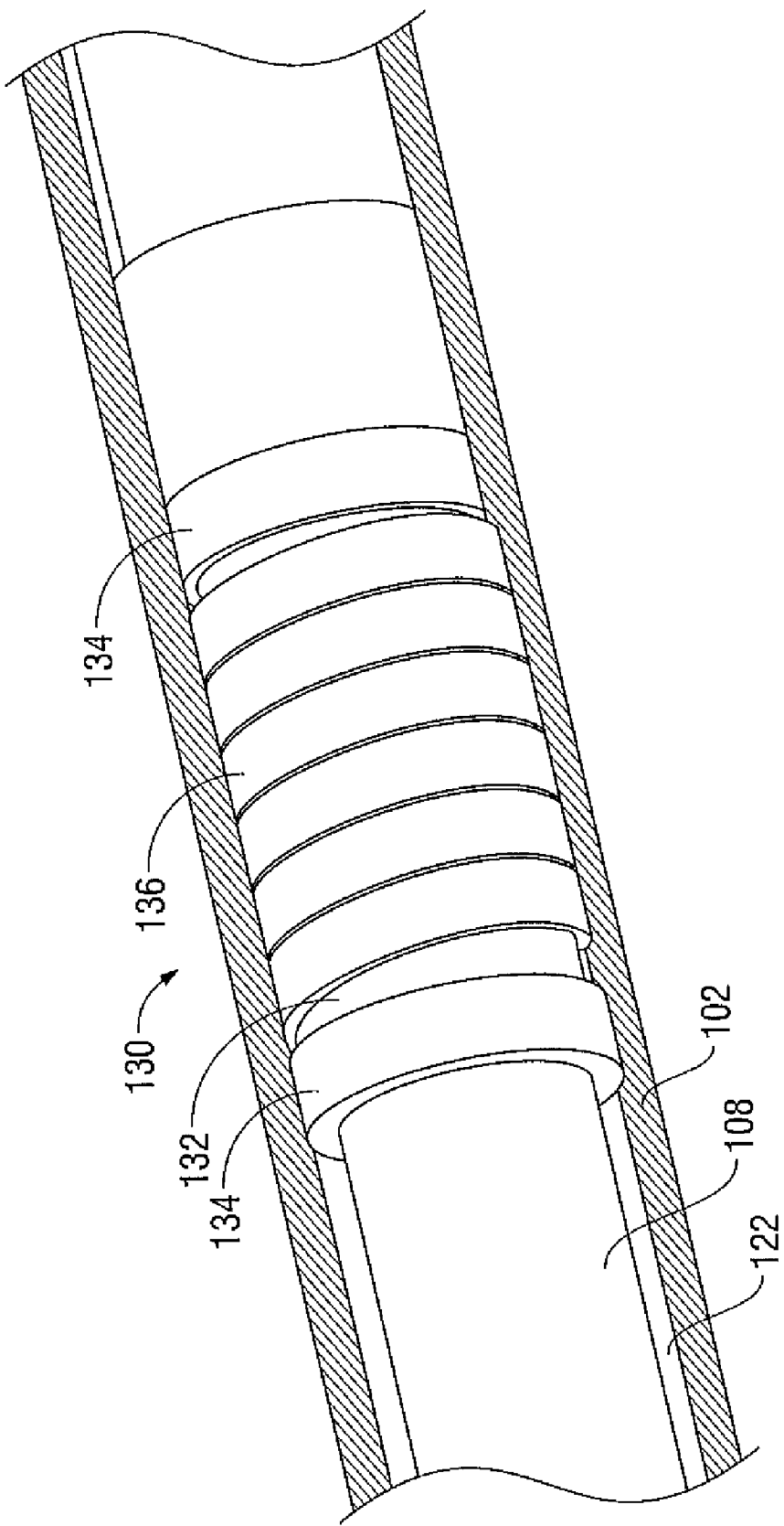

The slidable outer jacket 202 is adapted to slide along the cooling jacket 202 and the fluid feed member 208 from a closed configuration in which the slidable outer jacket 202 is mated with the trocar 125 and a retracted configuration in which the slidable outer jacket 202 is disposed a predetermined length alone the assembly 112 (e.g., half wavelength, quarter wavelength, etc.). The assembly 112 also includes a contact assembly 130 as shown in FIGS. 9-11 to provide electrical contact between the fluid feed members 206 and 208 and the sliding outer jacket 202.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:
1. A microwave antenna assembly comprising:
    a feedline including an inner conductor, an outer conductor and an inner insulator disposed therebetween;
    a radiating portion including a dipole antenna coupled to the feedline and a trocar coupled to the dipole antenna at a distal end thereof;

a slidable outer jacket disposed about the radiating portion and the feedline, the slidable outer jacket configured to slide about at least one of the radiating portion and the feedline from a closed configuration, in which the slidable outer jacket is mated with the trocar, and a retracted configuration, in which the slidable outer jacket is retracted proximally to expose at least a portion of the radiating portion; and a contact assembly disposed around the feedline and in electrical contact with the outer conductor, the contact assembly adapted to provide continuous electrical contact between the outer conductor and the slidable outer jacket, the contact assembly further comprising:

a tubular housing having at least two stop members each of which is disposed at a proximal distal end thereof, respectively; and a spring member disposed about the tubular housing between the at least two stop members, the spring member adapted to bias the slidable outer jacket.

2. A microwave antenna assembly according to claim 1, wherein the tubular housing and the spring member are formed from a conductive material.

3. A microwave antenna assembly according to claim 1, wherein the spring member is coated by a conductive coating having at least one metal compound.

4. A microwave antenna assembly according to claim 1, wherein the slidable outer jacket is formed from a conductive metal.

5. A microwave antenna assembly according to claim 1, wherein the slidable outer jacket includes a tapered edge at a distal end thereof and the trocar includes a tapered tip adapted to mate with the tapered edge when the slidable outer jacket is in the closed configuration.

6. A method for performing microwave ablation, the method comprising the steps of:

providing a microwave antenna comprising:

a feedline including an inner conductor, an outer conductor and an inner insulator disposed therebetween;

a radiating portion including a dipole antenna coupled to the feedline and a trocar coupled to the dipole antenna at a distal end thereof;

a slidable outer jacket disposed about the radiating portion and the feedline, the slidable outer jacket configured to slide about at least one of the radiating portion and the feedline from a closed configuration, in which the slidable outer jacket is mated with the trocar, and a retracted configuration, in which the slidable outer jacket is retracted proximally to expose at least a portion of the radiating portion; and a contact assembly disposed around the feedline and in electrical contact with the outer conductor, the contact assembly adapted to provide continuous electrical contact between the outer conductor and the slidable outer jacket, the contact assembly further comprising:

a tubular housing having at least two stop members each of which is disposed at a proximal end and a distal end thereof, respectively; and a spring member disposed about the tubular housing between the at least two stop members, the spring member adapted to bias the slidable outer jacket;

moving the slidable outer jacket into a closed configuration, in which the slidable outer jacket is mated with the trocar;

inserting the microwave antenna into tissue; and moving the slidable outer jacket into a retracted configuration, in which the slidable outer jacket is retracted proximally to expose at least a portion of the radiating portion.

7. The method according to claim 6, further comprising the step of:

maintaining continuous electrical contact between the outer conductor and the slidable outer jacket during the moving steps.

* * * * *